United States Patent [19]

Olivera et al.

[11] 4,447,356

[45] May 8, 1984

[54] CONOTOXINS

[76] Inventors: Baldomero M. Olivera, 1370 Bryan Ave., Salt Lake City, Utah 84105; Lourdes J. Cruz, 3993 Dangal, Sta Mesa, Manila, Philippines; William R. Gray, 3769 Parkview Dr., Salt Lake City, Utah 84117; Jean E. F. Rivier, 9674 Blackgold Rd., La Jolla, Calif. 92037

[21] Appl. No.: 385,125

[22] Filed: Jun. 4, 1982

Related U.S. Application Data

[63] Continuation-in-part of Ser. No. 255,237, Apr. 17, 1981, abandoned.

[51] Int. Cl.$^3$ ............................................. C07C 103/52
[52] U.S. Cl. ............................................. 260/112.5 R
[58] Field of Search ................................. 260/112.5 R

[56] References Cited

PUBLICATIONS

J. Biol. Chem. (1981) 256, 4734–4740.
Arch. Biochem. & Biophys. (1978) 190, 539–548.
Biochemistry, 684, 2171–2172.
J. Biol. Chem. 256, No. 10, (1981) 4734–4740.
FEBS Letters 148, No. 2, (1982) 260–262.

*Primary Examiner*—Delbert R. Phillips
*Attorney, Agent, or Firm*—Keil & Witherspoon

[57] ABSTRACT

The present invention provides bioactive peptides of generic formula $$U-Cys-Cys-V_4-V_5-V_6-Cys-W-X-Y-Z-V_{12}-Cys-R$$

with disulfide bonds S—S between the cysteines.

These peptides are extremely potent inhibitors of synaptic transmission at the neuromuscular junction, while at the same time lacing demonstrable inhibition of either nerve or muscle action potential propagation. The peptides are termed conotoxins herein. Naturally occurring conotoxins include conotoxin GI, GIA and GII. In conotoxin GI, U is Glu, $V_4$ is Asn, $V_5$ is Pro, $V_6$ is Ala, W is Gly, X is Arg, Y is His, Z is Tyr, $V_{12}$ is Ser and R is —NH$_2$. Conotoxin GIA is identical to GI except R is —Gly—Lys—NH$_2$. Conotoxin GII is identical to GI except that $V_4$ is His, Z is Phe, and X is Lys. Conotoxin MI is identical to GI except that U is Gly-Arg, X is Lys and Y is Asn.

15 Claims, No Drawings

CONOTOXINS

This application is a continuation-in-part of application Ser. No. 255,237, filed Apr. 17, 1981, now abandoned.

BACKGROUND AND PRIOR ART

Molluscs of the genus Conus produce a highly toxic venom which enables them to carry out their unique predatory lifestyle. Prey are immobilized by the venom which is injected by means of a highly specialized venom apparatus, described by Kohn, A. J., et al, *Ann.N.Y. Acad.Sci.*, 90, 706 (1960). The venom is injected into the prey by means of a disposable hollow tooth which functions both in the manner of a harpoon and a hypodermic needle. The most venomous of all Conus species is *Conus geographus* L., a fish-hunting species from the central Indo-Pacific. Its venom is so highly toxic that human fatalities have resulted from its sting. Another species, *Conus magus*, produces a conotoxin having a similar biological activity and structure.

Initial studies on the nature of *C. geographus* toxicity indicated that death was the result of acute muscle paralysis. Endean, R., et al. *Toxicon*, 14, 267 (1976) reported that *C. geographus* toxin inhibited the muscle action potential. Subsequently, attempts were made to fractionate and to partially purify active material from the crude venom (Spence, I., et al, *Life Sciences*, 21, 1759 (1977); Cruz, L. J., et al, *Arch.Biochem.Biophys.*, 190, 539 (1978)). Such studies revealed that *C. geographus* venom contains several toxic substances. These substances were shown to be peptides, although their structure was not determined. The toxic peptides of crude venom exhibit a variety of toxic effects. At least one has been found which inhibits muscle action potential. Others were found to act at the neuromuscular junction to inhibit the passage of an excitatory impulse across the junction, but which had no effect on muscle action potential. Conotoxin GI was mischaracterized in the prior art as a direct inhibitor of muscle contraction (Endean, et al, supra, and Cruz, et al, supra), because of the presence of contaminating substances in the toxin preparations.

The present invention discloses for the first time the biological activity and chemical structure of three homologous toxic peptides and their synthesis. The peptides are useful for the treatment of neuromuscular disorders and for rapid reversible immobilization of muscles in all vertebrate species, including humans, thereby facilitating the setting of fractures and dislocations. The toxins inhibit synaptic transmission at the neuromuscular junction and bond strongly to the acetylcholine receptor of the muscle end plate. The toxins are therefore especially suitable for detection and assay of acetylcholine receptors. Such measurements are of significance in clinical diagnosis of myasthenia gravis (Fambrough et al, Science 182 pp 293-295 (1973)). Toxin synthesized with radioactive label, or as a fluorescent derivative provides improved quantitation and sensitivity of acetylcholine receptor assays. All abbreviations used herein not otherwise identified are standard abbreviations approved for publication in the Journal of Biological Chemistry (all amino acids are in the L-configuration unless specifically stated otherwise).

SUMMARY OF THE INVENTION

The present invention provides bioactive peptides of generic formula $$U-Cys-Cys-V_4-V_5-V_6-Cys-W-X-Y-Z-V_{12}-Cys-R$$

with disulfide bonds S—S connecting the cysteines.

These peptides are extremely potent inhibitors of synaptic transmission at the neuromuscular junction, while at the same time lacking demonstrable inhibition of either nerve or muscle action potential propagation. The peptides are termed conotoxins herein. Naturally occurring conotoxins include conotoxin GI, GIA, GII and MI. In conotoxin GI, U is Glu, $V_4$ is Asn, $V_5$ is Pro, $V_6$ is Ala, W is Gly, X is Arg, Y is His, Z is Tyr, $V_{12}$ is Ser and R is —NH$_2$. Conotoxin GIA is identical to GI except R is —Gly—Lys—NH$_2$. Conotoxin GII is identical to GI, except that $V_4$ is His, X is Lys and Z is Phe. Conotoxin MI is identical to GI except that $V_4$ is His U is Gly—Arg, X is Lys and Y is Asn. A synthetic conotoxin, desGlu—GI, is identical to GI except that U is —NH$_2$. The biological activity of desGlu—GI is essentially the same as the naturally-occurring conotoxins.

Isolation, purification and structural determination of the foregoing conotoxins is disclosed herein. Further disclosed are the chemical synthesis of two conotoxins and demonstration of biological activity of the synthetic products.

The activity of the conotoxins is freely reversible upon dilution or removal of the toxin from the affected muscle. In addition, toxicity is destroyed by agents which disrupt disulfide bonds. The correct disulfide bonding pattern is essential for biological activity, and once disrupted does not spontaneously reform. The toxins are active on a wide range of vertebrate animals, including humans. The toxins are useful for reversibly immobilizing a muscle or group of muscles in humans or other vertebrate species. The toxins and derivatives thereof are further useful for detection and measurement of acetylcholine receptors.

An especially attractive feature of the peptides is the fact that they are sufficiently small to be chemically synthesized, while at the same time they present definable structural and steric requirements such that analogs and derivatives retaining biological activity can be synthesized following the teachings of the invention. Analogs having desired properties, such as reduced tissue mobility, can be synthesized, using the basic conotoxin structure defined herein.

DETAILED DESCRIPTION OF THE INVENTION

Biological activity of the conotoxins was measured by intraperitoneal injection into mice, as described by Cruz, et al, (1978), supra. One unit of activity is herein defined as the quantity needed to produce death in a 20-gram mouse, twenty minutes after injection.

Preliminary results revealed variable activity and toxin composition from one venom preparation to another. In some venom preparations, only conotoxin GI was detected, while in others, toxins GI, GIA and GII were all present. It is not presently known whether this polymorphism in toxin composition is genetic, due to changes in snail physiology or due to differences in venom extraction and storage. Previously published results could not be reproduced in detail since the mixture of toxic components varied from one preparation to the next. Following the prior art, purification from crude venom pooled from several snails yielded confusing and conflicting results, especially with respect to the amino acid compositions of the toxins. In an attempt to eliminate the inconsistencies of results obtained following the prior art, the techniques described therein (Cruz, et al, (1978), supra) were scaled down to enble purification from a single snail. Surprisingly, consistent results enabling characterization of the toxins were then obtained. Therefore, proper characterization of the toxins was frustrated until techniques were developed to isolate and characterize venom from a single snail. In addition, it was discovered that reverse-phase high performance liquid chromatography (HPLC) was capable of completely resolving conotoxins GI and GII, which were not resolvable by the prior art phosphocellulose chromatograhy (Cruz, et al, supra). HPLC is preferred for purification of all the conotoxins disclosed herein, as exemplified by its use in the purification of conotoxin MI.

Methods of venom extraction and partial purification have been previously described (Cruz, L. J., (1977), and Cruz, L. J., et al (1978), supra). However, in the work described herein, either the methods were scaled down to enable purification from an individual snail, or the toxins were purified by HPLC. Further purification by phosphocellulose chromatography and paper electrophoresis were also developed, as described in the accompanying Examples.

The amino acid sequences of conotoxins GI, GIA and GII are based upon sequence data as described in the Examples. Because the amounts obtainable from individual snails are small, usable amounts of the desired toxins can only be obtained by chemical synthesis, as a practical matter. For example, the yield from a single snail (which can only be used once) is less than 100 micrograms of toxin. Furthermore, the snails are difficult to obtain. They must be collected by hand by divers working at night, in depths averaging 30 feet, in Pacific waters near the Philippines. The amount which can be obtained from these sources are sufficient for analytical purposes but are not sufficient for any practical use. Chemical synthesis of biologically active toxin depends not only upon correct determination of the amino acid sequence, but also on formation of the correct disulfide bond pairs. The active conformation is not thermodynamically favored under normal physiological conditions, so that the correct disulfide pairing does not occur spontaneously. Therefore, to be of practical utility, the chemical synthesis of the toxins must be carried out so as to provide not only the correct amino acid sequence but also the correct disulfide pairing.

All the toxins are markedly basic peptides, highly folded when correctly cross-linked. All have approximately the same level of activity, suggesting a reasonable tolerance for substitution at the carboxy terminus.

The presence of four cysteine residues and the ability to destroy biological activity by agents which break disulfide bonds, such as sodium borohydride or β-mercaptoethanol, indicates that a specific folded configuration induced by disulfide cross-links is essential for activity. Furthermore, once reduction of disulfide bonds of the active toxin has occurred, reoxidation does not result in significant reactivation of toxic activity. Therefore, biological activity is dependent upon a unique pairing of the proper sulfhydryl groups, which pairing does not occur as a result of spontaneous folding of the petide under normal conditions. Characterization of the active form of the toxins involved determination of the correct disulfide combination, as described, infra. Similarly, synthesis of active toxin required specific methodology designed to achieve the desired pairing.

The data presented herein on the structure and physiological activity of the conotoxins makes it possible to determine which parts of the sequence are critical to biological activity, thereby permitting the synthesis of analogs and derivatives having similar activities by providing additionally useful properties. Such modified toxins including those having enhanced stability, sustained released, improved tissue localization, and the like. Comparisons of the sequences of five conotoxins having essentially the same biological activity reveals the permissibility of certain amino acid substitutions, in particular at positions 4–6 and 8–12, and in the carboxy terminal blocking group.

The conotoxins inhibit synaptic transmission at the neuromuscular junction by binding the acetyl choline receptor at a muscle end plate. X-ray crystallographic data have established the three-dimensional structure of erabutoxin, a protein toxin of sea snake venom which also binds to the acetyl choline receptor of the muscle end plate. At the same time, the sequence data disclosed herein together with the specific disulfide cross-linking required for activity of the conotoxins has permitted the construction of molecular models of the conotoxins. The disulfide cross-links produce a very tightly folded structure which correlates extremely well with the conformation of the active portion of erabutoxin and provides certain essential similarities thereto, with respect to the three-dimensional positioning and orientation of certain functional groups. Such groups are those considered to be most important for the biological function of both conotoxins and erabutoxin. Structural modifications of the conotoxins which retain the same or similar three-dimensional orientation and positioning of these major functional groups can be derived, with the aid of molecular models. On the basis of such structural and physiological evidence, a generic conotoxin sequence is defined as follows:

$$U—Cys—Cys—V_4—V_5—V_6—Cys—W—X—Y—Z—V_{12}—Cys—R$$

wherein U is $—NH_2$, Glu, Asp, any D- or L-amino acid having a free or substituted amino group such as N-trimethyl-Glu or N-trimethyl-Asp, or any short chain peptide of two to four amino acids having a positively charged group, such as Gly—Arg; V is any L-amino acid; W is glycine or any D-amino acid; X is lysine, arginine, or a positively charged L-amino acid, such as ornithine, homoarginine, N-methyl-lysine, dimethyl lysine, or trimethyl lysine; Y is any L-amino acid including asparagine, histidine, phenylalanine, tyrosine, or other aromatic amino acid such as nitrotyrosine or monoiodo histidine; Z is leucine, valine, isoleucine, phenylalanine, tyrosine, or an aromatic or bulky hydrophobic amino acid such as cyclohexylalanine, monoiodotyrosine, diiodotyrosine, or monochloromonoiodotyrosine; and R is any carboxyl group blocking agent including $—NH_2$, $—Gly—Lys—NH_2$, an oligopeptide, a protein, alkyl, aryl, cycloalkyl groups, and branched and substituted derivatives thereof. It will be understood that all positively or negatively charged are so defined with respect to conditions if pH is at or near normal physiological conditions, i.e., from about pH 6.5 to about pH 8.5.

Substitutions in position 1 (also designed U herein) are permissible to the extent they retain the positive charge of the N-terminal amino acid without providing an overly bulky group, based upon comparison with the three-dimensional structure of the active site of erabutoxin. A free —$NH_2$ group on the Cys residue of position 2 is sufficient, since desGlu—GI is fully active. The cysteine resides in positions 2, 3, 7 and 13 are required to provide the disulfide cross-links necessary to maintain an active configuration for the conotoxin peptide. The active peptide has disulfide bonds pairing residues 2 and 7 and residues 3 and 13. Other pairings are inactive. Any L-amino acid may be provided in positions 4, 5, 6, 10 and 12. In position 8, the steric requirements of the model are such that only glycine among the naturally-occurring amino acids may be inserted. However, any D-amino acid may be inserted at position 8 since the side chains will be oriented in the opposite direction and no steric hinderance will be encountered. Substitution of a D-amino acid in position 8 is considered advantageous since it is known that peptides containing D-amino acids are resistant to proteolytic degradation. In position 9, the structural studies comparing conotoxins GI, GII and GIA indicate that either arginine or lysine may be inserted. Comparison with the three-dimensional structure of the erabutoxin active site indicates that a positively-charged side chain is a necessary component for biological activity.

At position 10, comparison with short snake neurotoxins, including erabutoxin, indicates that His and Phe both give biological activity. Long snake neurotoxins, such as α-bungarotoxin, have additional residues in this area, but maintain an aromatic residue (Phe or Trp) at the equivalent position. However, conotoxin MI has Asn at position 10, indicating that other L-amino acids may be substituted without loss of activity. The steric requirements are such that the positively-charged amino acid must be in the L-configuration. In position 11, comparison with erabutoxin indicates the desirability of either an aromatic or bulky hydrophobic side chain. Comparative sequence studies and comparisons between conotoxin molecular models and the three-dimensional structure of erabutoxin indicate that virtually any carboxyl blocking group regardless of size may be employed. From the structures of conotoxins GI, GII and GIA, it is evident that amino groups and dipeptide amide blocking groups are permitted structural variants. Furthermore, from the erabutoxin structure it is apparent that the bulk of the erabutoxin molecule occupies the position of the R group of conotoxin. Therefore, the R group may be quite large and may in fact be a protein. The only limitations on the nature of the R group will be based on considerations known and understood by those of ordinary skill in the art. For example, blocking groups having regions incompatible with biological tissues or groupings which confer inappropriate solubility characteristics of the molecule as a whole. By the same token, it will be readily appreciated that the nature of R may be varied to build in desirable properties for the toxin molecule including limited tissue mobility and timed-release properties.

The examples which follow demonstrate purification of biologically active conotoxins to a degree sufficient to permit amino acid sequence analysis. The biological activity and mode of action of the toxins are demonstrated. Chemical synthesis of a conotoxin and demonstration of biological activity of synthetic toxin are also demonstrated.

EXAMPLE 1

Crude venom from a single snail (*Conus geographus*) was extracted and lyophilized, essentially as described by Cruz, L. J., et al, supra. Lyophilized venom from a single snail was extracted with 0.3 ml of 0.01 M N-ethyl morpholine acetate (NEMAC), pH 9.0. The extract was then applied on a 10×0.5 cm column of phosphocellulose previously equilibrated with the same buffer. Elution was carried out first with a linear gradient of 30 ml 0.01 M NEMAC, pH 9.0 and 30 ml of 0.6 M NEMAC, pH 9.0, followed by another gradient with 30 ml of 0.6 M and 30 ml 2.0 M NEMAC, pH 9.0, as limiting buffers. The results are shown in FIG. 1. Total protein was assayed as described by Cruz, L. J., et al, supra. Biological activity was approximately located by pooling small samples from several fractions and testing, in the described mouse assay. More precise location was made by assaying individual fractions through areas of interest. Conotoxin activity was found in peaks A and B. Peak A was found by subsequent analysis to contain two conotoxins, GI and GII, while Peak B, eluting at about 0.8 M NEMAC, contained conotoxin GIA.

Conotoxins GI and GII were separated by paper electrophoresis at pH 5.4. Material from the central region of Peak A in FIG. 1 was subjected to electrophoresis in 0.2 M pyridine acetate buffer, pH 5.4, for two hours, twenty minutes at 27 volts per centimeter. Guide strips were cut from the edges of the peptide zones and stained with ninhydrin (for amino groups), Pauli stain (for His and/or Tyr), Sakaguchi stain (for Arg), and Ehrlich's stain (for Trp), as described by Bennett, J. C., *Methods Enzymol.*, 11, 330 (1967). The staining results are shown in FIG. 2A, indicating two staining regions having different amino acid compositions. Conotoxin GI was shown to contain arginine, while conotoxin GII lacked arginine (see FIG. 2A). In FIG. 2B, the peptides were eluted from the unstained regions of the paper and were tested by bioassay and amino acid analysis. The quantitative relationship between activity of peptide and in the eluted strips is very strong confirmatory evidence that the peptides are the active molecules. From the curves, the specific activities of GI and GII are 5.2 and 3.7 units for nmole, respectively.* The specific activity of conotoxin GIA is roughly equivalent, on a molar basis.

*These values, as published, were based on incorrect assessment of the yield of peptide. Current analyses indicate the correct values to be 1.5 and 1.1 units, respectively.

EXAMPLE 2

Amino acid composition. Samples of toxin were lyophilized, then hydrolyzed in vacuo, using redistilled, constant-boiling HCl (approximately 6 N), at 105° C. for twenty hours. After removal of Hcl over NaOH in vacuo, the samples were analyzed on a Beckman model 121C amino acid analyzer (Beckman Instruments, Fullerton, Calif.) essentially as described by Spackman, D. H., et al, *Anal.Chem.*, 30, 1190 (1958). The results are shown in Table 1. Amino acid composition of conotoxin GI was previously reported by Cruz, et al (1978). The numbers in parentheses indicate corrected whole number mole ratios of each residue, per mole of toxin.

The identification of amino-terminal amino acids is carried out by the Dansyl chloride provedure of Gray, W. R., *Methods Enzymol.*, 11, 139 (1967). Dansyl amino acids (hereinafter DNS— followed by the amino acid symbol) were identified by high-voltage electrophoresis at pH 4.4 for two or three hours at 54 v/cm supplemented by electrophoresis at pH 1.7 for one to 1.5 hours at 45 v/cm. Conotoxins GI, GII and GIA showed DNS—Glu as the only α-labelled amino acid. Enzymatic digestion with aminopeptidase M released Glu as the only free amino acid from an equimolar mixture of GI and GII (0.6 moles per mole of peptide). Therefore, glutamic acid was identified as the N-terminal amino acid of each of the three toxins.

Initial experiments to determine the carboxy termini of GI and GII revealed that less than 0.05 moles per mole was released from both native and performic acid oxidized toxins under conditions in which insulin, as a control, was extensively degraded. Similarly, hydrazinolysis of native and oxidized GI did not yield significant amounts of free amino acids, in comparison with controls. It was therefore concluded that the carboxyl termini were blocked, i.e., were not present as a free carboxyl group.

EXAMPLE 3

Sequence determination. Sequence analysis was carried out either by the Dansyl-Edman method (Gray, W. R., *Methods Enzymol.*, 11, 469 (1967)), or by the use of the Beckman 890B Sequenator (Beckman Instruments, Fullerton, Calif.), as described by Edman, P., et al, *Eur.J.Biochem.*, 1, 80 (1967), using a single-cleavage program with dimethylallylamine buffers. In the case of GIA, sequenator analysis was carried out in the presence of Polybrene, as described by Tarr, G. E., et al, *Anal.Biochem.*, 84, 622 (1978). Amino acid phenylthiohydantions (hereinafter PTH-amino acid) were identified by high performance liquid chromatography on columns of ODS—silica (du Pont Corporation, Wilmington, Del.); the gradient used for elution was essentially that described by Hunkapiller, M. W., et al, *Biochem.*, 17, 2124 (1978). Stepwise application of the dansyl-Edman procedure on a mixture of GI and GII gave the following sequence:

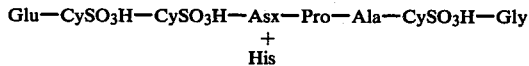

Trypsin digestion of a mixture of GI and GII resulted in the appearance of His as the only new end group revealed by dansylation. Between 10 to 100 nmoles of peptide were incubated at 37° C. for four hours in 100 ml of a solution of trypsin (0.2 mg/ml) in 0.2 M NEMAC buffer, pH 8.5. The digested material was oxidized with performic acid according to the method of Hirs, C. W. H., *Methods Enzymol.*, 11, 197 (1967), using pre-formed performic acid, cooled to 0° C. After reaction for thirty minutes at 0° C., samples were diluted twenty-fold with distilled water and lyophilized. They were then re-dissolved in water and lyophilized a second time to remove further traces of acid. The trypsin-digested performic acid-oxidized fragments were separated by high voltage electrophoresis at pH 6.4 for 2.5 hours at 28 v/cm. A cooled flat-plate apparatus was used. Samples were run on Whatman No. 3MM paper with 0.1 M pyridine acetate, pH 6.4. Samples were applied as streaks at a loading of approximately 10–20 nmoles/cm, and guide strips were cut from the edges for staining. Small amounts of DNS—NH₂ and DNS—OH were included as mobility markers, and as guides for cutting strips for subsequent elution of peptides. (DNS—OH is 1-dimethylaminonaphthalene-5-sulfonic acid, commonly termed dansyl sulfonic acid; DNS—NH₂ is 1-dimethyl-aminonaphthalene-5-sulfonamide, commonly termed dansyl amide). Three fragments were observed upon electrophoresis, two anodally moving bands and a neutral band. Each band was eluted and subjected to amino acid analysis and dansyl-Edman degradation, as previously described, yielding the following results:

(1) Faster anodal band.
Composition—1 Arg, 1 Asx, 1 Glx, 1 Pro, 3 CySO₃H, 1 Gly, 1 Ala.
Sequence—Glx—CySO₃H—CySO₃H—Asx—Pro—Ala—CySO₃H—Gly (Arg)

On the basis of a measured net charge of −3, and the established status of the Glu residue at position 1, the residue at position 4 was identified as Asn rather than Asp.

(2) Slower anodal band.
Composition—1 Lys, 1 His, 1 Glx, 1 Pro, 3 CySO₃H, 1 Gly, 1 Ala.
Sequence—Glx—CySO₃H—CySO₃H—His—Pro—Ala—CySO₃H—Gly—Lys The net charge of that peptide was between −2 and −3, compatible with the assignment of Glu as the amino terminal residue.

(3) Neutral band.
Composition—1 His, 1 Ser, 1 CySO₃H, 0.5 Phe, 0.3 Tyr.

Degradation of this peptide established clearly that it was a mixture of His—Tyr—(Ser, CySO₃H) and His—Phe—(Ser, CySO₃H). Further experiments following conventional analytic techniques to determine the sequence at the carboxy terminus resulted in highly anomalous behavior, indicating that chemical rearrangements were occurring. It was therefore necessary to resort to other techniques, described infra, to resolve the sequence at the carboxy terminus.

Sequential degradation of GIA. A sample of GIA was reduced and selectively S-methylated with methyl P-nitrobenzene sulfonate according to the procedure described by Hendrikson, R. L., *J.Biol.Chem.*, 246, 4090 (1971). An approximately 120 nmole sample of reduced and S-methylated GIA was analyzed in the Sequenator. The sequence of the first 11 residues was found to be identical with that of the first 11 residues of GI:

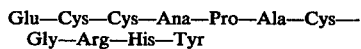

This experiment left unassigned four residues: Ser, Cys, Gly and Lys.

Because conventional sequence analysis yielded an anomalous result for the carboxy terminal sequence, alternative techniques were devised to characterize the sequence. For these investigations it was found convenient to label Cys residues using ¹⁴C-iodoacetate, using a commercial preparation of specific activity 54 mCi/mmole. Samples of peptide were first reduced using a 2.5 fold excess of β-mercaptoethanol in 0.5 M Na borate, pH 7.7, at 50° C. for two hours. Undiluted ¹⁴C-iodoacetate was then added and allowed to react for one hour at room temperature. This was followed by reduction using a further five-fold excess of mercaptoethanol at 50° C. for thirty minutes, and finally by addition of a four-fold excess of ¹²C-iodoacetate over total—SH groups. After thirty minutes at room temperature, a four-fold excess of β-mercaptoethanol was added and allowed to react for thirty minutes. The sample was then freeze-dried and redissolved in $H_2O$. The carboxymethylated peptide was purified by high-voltage electrophoresis at pH 1.7 (7% v/v formic acid) for 1.5 hours at 44 v/cm. Throughout the labelling reactions, the samples were kept dark by wrapping the tube with aluminum foil. Control experiments with vasopressin established that these conditions gave high labelling with minimum side reactions. Sodium borate was used as the buffer because NEMAC and pyridine gave rise to laballed products, presumably by alkylation of the tertiary nitrogens.

A sample of 25 nmoles of GI was alkylated as described in the preceding paragraph. The labelled peptide was cleaved by digestion with chymotrypsin under conditions previously described for trypsin digestion, followed by electrophoresis of the fragments in 0.2 M NEMAC, pH 8.0 at 18 v/cm for eight hours. Two radioactive bands were obtained. Three-fourths of the radioactivity was in a band running towards the anode, presumably the amino terminal undecapeptide containing three residues of $14_C$-carboxymethylcysteine. The remaining one-fourth was in the neutral band, presumably representing the carboxy terminal dipeptide derivative. Material in the neutral band was eluted and subjected to various experiments as described, infra, with unlabelled carboxymethyl cysteine added as carrier to minimize oxidative losses.

In the first experiment, the C-terminal dipeptide was acid-hydrolyzed, followed by electrophoresis at 6.4. All radioactivity migrated with carboxymethyl cysteine. Therefore, all labels incorporated at the cysteine residue, as expected.

In the second experiment, the carboxy terminal dipeptide derivative was dansylated, followed by hydrolysis and electrophoresis at pH 1.7. A trace of DNS—Ser was obtained. All radioactivity migrated with free carboxymethyl cysteine. These results suggested serine as the penultimate residue.

In the third experiment, the dipeptide was oxidized by a periodate, by modification of the method of Dixon, H. B. F., *Biochem.J.*, 83, 91 (1962), using 25 μl of 0.1 M and 0.5 M $NaIO_4$ in 0.05 M potassium phosphate buffer, pH 7.05 at room temperature for one hour. The treatment resulted in a shift from a net positive to a zero charge at pH 1.7. Controls on several other small peptides confirmed that only those containing amino terminals Ser or Thr are affected by this treatment.

The $^{14}C$-carboxymethylated dipeptide (2,000 cpm) was incubated at 37° C. for 12 hours in 25 ml of a 1 mg/ml pronase solution in 0.2 M NEMAC, pH 8, and 1 mM $CaCl_2$. The reaction mixture was dried under vacuum, redigested with the same amount of enzyme for an additional three hours, and dried again before electrophoresis. Electrophoresis was carried out at pH 6.4 (0.1 M pyridine acetate) in the presence of carboxymethyl cysteine (CMCys), carboxymethyl cysteine α-methyl ester (CMCys—OMe), carboxymethyl cysteine α-amide (CMCys—$NH_2$), and undigested dipeptide. At pH 6.4, the original dipeptide, the pronase-digested material and the amide and ester derivatives of carboxymethyl cysteine remained at the neutral point. However, upon electrophoresis at pH 1.7 (7% v/v formic acid) the pronase-digested material ran rapidly toward the cathode and comigrated with CMCys—$NH_2$. The mobility of the radioactively-labelled, pronase-digested material was quite distinctive, greater than that of undigested peptide and of CMCys, less than that of CMCys—OMe, and identical with CMCys—$NH_2$. From the mobilities of digested and undigested peptides relative to that of DNS—$NH_2$, an upper limit of approximately 40 to 50 daltons is set for the weight of the group blocking the carboxyl group of the toxin. Methyl ester is excluded from the data, while ethyl ester is compatible with the results. However, the foregoing data indicate that the blocking group is amide, which is consistent with the fact that the amide group is the only common carboxy terminal block encountered in natural peptides.

The foregoing results indicate that the C-terminal sequence of GI and GII is —Ser—Cys—$NH_2$.

C-terminal sequence of GIA. Conotoxin GIA was reduced and carboxymethylated with $^{14}C$-iodoacetate as previously described. Chymotrypsin cleavage of the carboxymethylated peptide yielded two radioactive fragments, the first was negatively charged and contained about three times as much radioactivity as the second, positively charged fragment. Amino acid analysis indicated that the second fragment was a tetrapeptide containing Ser, CysCM, Gly and Lys. A measured charge of +1.0 indicated that the carboxyl terminus is blocked.

Dansylation and hydrolysis of the carboxylmethylated tetrapeptide yielded DNA—Ser and ε—DNS—Lys, confirming that Ser is amino terminal.

The tetrapeptide was digested with the enzyme dipeptidylaminopeptidase I, commercially available from Sigma Chemical Company, St. Louis, Mo. Following the procedure of Callahans, P. X., et al, *Methods Enzymol.*, 25, 282 (1972), approximately 2.5 nmoles of peptide were dried in a small Pyrex tube of the type used for dansylation. The peptide was then dissolved in 25 ml of 0.05 M pyridine acetate buffer, pH 4.5 containing 5 mM EDTA, 15 mM β-mercaptoethanol, and 1% (w/v) NaCl. Digestion was started by the addition of 2.5 ml (0.02 units) of enzyme dissolved in water. After reaction for 0.5 to 2 hours at 37° C., samples were dried in vacuo, and dansylated in the usual manner. Controls were run in which enzyme alone was incubated and dansylated; insignificant quantities of dansyl amino acids were produced. Based on the known specificity of the enzyme, two dipeptides resulted from cleavage of the tetrapeptide. The radioactive dipeptide was negatively charged. Dansylation and hydrolysis of the radioactive peptide gave DNS—Ser. Periodate oxidation of the dipeptide resulted in a product which was neutral at pH 1.7. Thus, the second residue from the N-terminus is Cys. Dansylation of both the dipeptide products of dipeptidylaminopeptidase I treatment, followed by hydrolysis, yielded DNS—Ser, ε—DNS—Lys and DNS—Gly. There was no trace of either α— or bis—DNS—Lys. The tetrapeptide was also subjected to trypsin digestion, under conditions described previously. A 10 nmole sample of tetrapeptide was trypsin-treated and subjected to electrophoresis at pH 6.5. Only the neutral radioactive band showed ninhydrin reactivity. No ninhydrin staining material was found at the position of glycinamide. Hydrolysis of material eluted from the neutral band showed all four amino acids as major components, but there was sufficient contamination in this experiment to preclude a definitive test of whether Gly was truly an integral part of the digested peptide.

The foregoing results taken together strongly suggest that the sequence of the C-terminal peptide of GIA is Ser—Cys—Gly—Lys—$NH_2$. Identification of amide as the carboxyl blocking group is based on electrophoretic mobility data indicating very low molecular weight and ready removal by trypsin.

Specificity of disulfide cross-links. No significant amounts of free-SH were found in GI or GII. From the molecular weight of 1500 daltons (Cruz, L. J., et al, (1978)), it must be concluded that the toxins exist as monomers containing two internal disulfide bridges. Biological activity of the conotoxins depends upon maintenance of a specific folded configuration for the toxin molecule, which configuration is maintained by the disulfide bridges. The correct disulfide pairing has been determined to be between positions 2 and 7, representing one pair, and positions 3 and 13, representing the other pair. Unpaired and mispaired disulfides result in loss of activity.

The disulfide pairings were analyzed by Edman degradation under conditions which did not reduce, oxidize or rearrange the disulfide bonds. Control experiments showed that toxin retained full activity upon exposure to the reaction conditions of Edman degradation in the absence of the phenylisothiocyanate reagent, while the reagent itself is known to leave disulfide bonds intact. After the first round of conventional Edman degradation to remove the N-terminal Glu, the Cys at position 2 was treated with radioactive phenylisothiocyanate. The second round of cleavage was followed by digestion with trypsin or chymotrypsin at pH 6.5. The results of enzymatic digestion differ depending on whether the Cys residue at position 2 is joined in disulfide linkage to the Cys at position 7 or position 13. If Cys 2 is joined to Cys 7 and Cys 3 is joined to Cys 13, the cleavage by trypsin or chymotrypsin yields a single molecule, but if Cys 2 is joined to Cys 13, and Cys 3 to Cys 7, the cleavage results in two peptides; if Cys 2 is paired to Cys 3, and Cys 7 to Cys 13, the enzymic cleavage yields a single peptide. These alternatives are distinguishable by high-voltage electrophoresis of the enzymatic cleavage products. The two possible alternatives yielding a single enzymic cleavage product after two cycles of Edman degradation (removing Glu—Cys—Cys) followed by trypsin or chrymotrypsin cleavage. If the pairing is Cys 2 to Cys 3 and Cys 7 to Cys 13, a single cleavage product results; however, if the pairing is Cys 2 to Cys 7, and Cys 3 to Cys 13, enzyme cleavage yields two peptides. Experiments based on the foregoing analysis indicate that the correct pairing is 2 to 7 and 3 to 13. These pairing assignments have been confirmed by chemical synthesis of active contoxin, as described, infra.

EXAMPLE 4

Physiological action. The physiological mode of action of conotoxins GI, GII and GIA was studied in an isolated neuromuscular preparation. The cutaneous pectoris muscle of small grass frogs (*Rana pipiens*) was dissected. The muscle was excited, either by directly depolarizing the major nerve innervating this muscle using a suction electrode (2 V), or by impaling the muscle with a micropipette filled with 0.5 M $K_2SO_4$. The transmembrane potential was measured by using another micropipette. For most experiments, normal frog's Ringer's solution was used, containing 120 mM NaCl, 2.5 mM KCl, and 1.8 mM $CaCl_2$, using piperazine-N,N'-bis (2-ethane sulfonic acid) (PIPES) buffer, pH 7.2–7.3, and 10 mM phenol red as a pH indicator. This solution also contained glucose, 0.5 g/l. For some experiments a high $Mg^{++}$, low $Ca^{++}$ Ringer's solution was used, containing 113 mM NaCl, 2.5 mM KCl, 5 mM Tris-maleate, pH 7.4, 0.5 mM $CaCl_2$, 5 mM $MgCl_2$. All experiments were performed at 15°-20° C. The muscles were observed under the microscope, and twitching was monitored by visual inspection. The results obtained under various conditions of stimulation in the presence and absence of conotoxin indicate that conotoxins GI, GII and GIA all act at the muscle end plate region. There was no detectible inhibition of either nerve or muscle action potential propagation at the toxin concentrations used. The post-synaptic effects are sufficient to account for the potent biological activity of these peptides. These results are consistent with the conclusion that the toxins exert their action by binding to the acetylcholine receptor of the muscle end plate.

Toxicity studies were carried out as described previously, using the mouse assay. The specific activity of purified GI and GII are approximately 5.2 and 3.7 units per nmole, respectively. The specific activity of GIA is roughly equivalent, on a molar basis, to that of the other toxins.

EXAMPLE 5

Synthesis of conotoxin GI. Toxin was synthesized by stepwise elongation from the carboxyl terminus, using the solid phase peptide synthesis procedure essentially as described by Merrifield, *J. Am. Chem. Soc.*, 85, 2149 (1964). Operational details of the procedure, which is well-knwon in the art, can be found in Stewart, J. M. and Young, J., *Solid Phase Peptide Synthesis*, Freeman & Co., San Francisco, Calif. (1969). A benzyhydrylamine resin was used as the solid phase support, to facilitate production of the amide form of the peptide.

Amino acid residues, in the form of their t-BOC derivatives, were coupled successively to the resin using dicyclohexylcarbodiimide as the condensing agent. At each cycle of stepwise amino acid addition, the t-BOC group was removed by acidolysis with 50 percent (v/v) trifluoroacetic acid in methylene chloride, using an appropriate scavenger, exposing a new amino group for subsequent coupling.

With one exception, described below, the side chain protecting groups were chosen from the standard set of moderately acid-stable derivatives. Such protecting groups are not removed during deblocking by trifluoroacetic acid in methylene chloride, but all are cleaved efficiently by anhydrous HF to release the functional side chains. Cysteine residues in positions 2 and 7 of the peptide were protected by S-p-methoxy-benzyl groups so as to expose sulfhydryls upon deprotection. The exception to the HF-cleavable blocking groups was used for the second pair of cysteine residues, those in positions 3 and 13. These groups were protected as the acetamidomethyl derivatives, providing complete stability towards HF.

The linear peptide was cleaved from the resin and deprotected with HF under standard conditions, removing all but the acetamidomethyl protecting groups.

Formation of the specific disulfide crosslinks was carried out in a cyclization reaction, carried out on the crude peptide product in liquid phase reactions. The first cyclization step, joining Cys 2 to Cys 7, was carried out by oxidation using potassium ferricyanide, as described by Rivier, J., et al, *Biopolymers*, 17, 1927 (1978). After formation of the first disulfide bridge, as described, the protecting acetamidomethyl groups were removed oxidatively using $I_2$, with concomitant disulfide bridge formation between Cys 2 and Cys 13, according to the method of Kamber, et al, *Helv. Chem. Acta,* 63, 899 (1980).

The resulting peptide was purified to homogeneity using high-performance liquid chromatography on reverse-phase supports. Starting with 5 g of resin, a yield of about 100 mg purified peptide could be obtained. The product was characterized by amino acid analysis and by toxicity tests. One microgram of the synthetic toxin injected intraperitoneally in a mouse was lethal in less than 10 minutes. The synthetic product is therefore highly toxic, and synthesis by the described method confirms the disulfide pairing assingments considered to be essential for biological activity.

The method for achieving correct disulfide pairing yields a key intermediate having the generic structure:

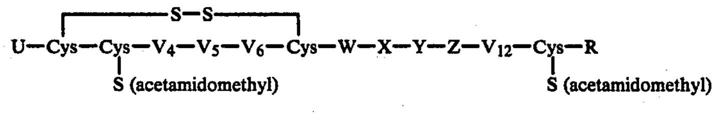

In the case of conotoxin GI, the sequence is:

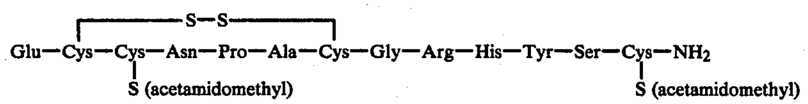

Alternatively, if the opposite disulfide pair is first cyclized, the key intermediate will have the generic structure:

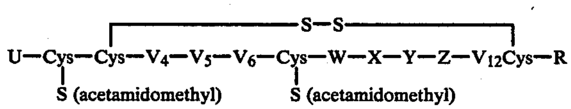

In the case of conotoxin GI, the sequence is:

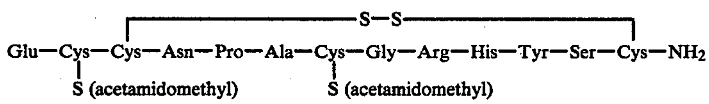

EXAMPLE 6

Conotoxin MI. Crude venom from *Conus magus* was first fractionated on a 2.5 cm×92 cm column of Sephadex G-50 (trademark, Pharmacia, Inc., Uppsala, Sweden) eluted with 1.1% (v/v) acetic acid. Active fractions, identified by bioassay as described supra, was pooled, lyophilized and chromatographed on phosphocellulose at pH 9.0, essentially as described in Example 1. Further purification of conotoxin MI was carried out by reverse-phase high performance liquid chromatography (HPLC). See Rivier, J., *Liq. Chrom.,* 1, 343 (1978). HPLC is the preferred method for purification of all the conotoxins described herein.

All experiments described herein was performed using a Hewlett-Packard Model 1084B instrument with a VYDAC C18 column (0.46 cm×25 cm 5 particle size) at a flow rate of 1.5 ml/min. To facilitate subsequent bioassays, a volatile buffer system containing trifluoroacetic acid (TFA) in a gradient of acetonitrile was employed. In some experiments, described infra, 0.5% (v/v) TFA was employed. The column effluent was monitored by absorbance at 210 nm. Linear gradients were formed by mixing solvent A, 0.1% (v/v) TFA and solvent B, 0.1% (v/v) TFA in 60% (v/v) acetonitrile. Linear segments of the gradient are presented herein as %B (v/v) achieved at times (minutes) given in parentheses, typically 10(0)-10(2)-35(25). Alternatively, a gradient of acetonitrile in 0.1% (v/v) triethylammonium phosphate (TEAP) pH 3 was employed, typically 2.4% (v/v)-48% (v/v) in 40 minutes.

The amino acid composition and amino acid sequence of purified conotoxin MI were determined essentially as described in Examples 2 and 3. The amino acid sequence of conotoxin MI is:

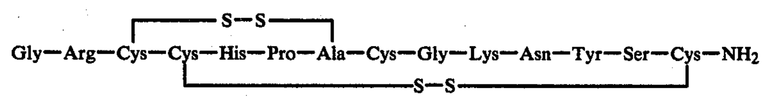

Conotoxin MI was synthesized following the same general synthetic approach described in Example 5. The peptide was built stepwise from the carboxyl terminus on a benzhydrylamine resin, using Acm as the protecting group for Cys 4 and Cys 14, and benzyl as the protecting group for Cys 3 and Cys 8. Peptide was released from the resin as the C-terminal amide, by treatment with anhydrous HF. In this step, Cys 3 and Cys 8 were deprotected: the corresponding disulphide bridge was closed by oxidation with ferricyanide, under conditions of "infinite dilution" of peptide. The monocyclic peptide intermediate was purified by reversed-phase HPLC in the TEAP—acetonitrile system (7), and then was desalted using 0.1% TFA—acetonitrile. Oxidative closure of the second disulphide bridge was carried out using $I_2$ in acetic acid (8). Chromatography of the bicyclic peptide product in both TEAP—acetonitrile and 0.1% TFA—acetonitrile gave highly asymmetrical peaks; a broad, gently sloping leading edge led to a relatively sharp peak at the trailing edge. Material from the sharp portion of the peak had the expected amino acid composition, and was used for the experiments described below.

Reversed-Phase HPLC of Natural and Synthetic Conotoxin MI. Except as noted, all HPLC analyses were carried out as described supra, using either 0.1% TFA—acetonitrile, or 0.5% TFA—acetonitrile. The column effluent was monitored by absorbance at 210 nm. Analyses were made at several temperatures, to improve peak characteristics.

Enzymatic Digests of Natural and Synthetic Conotoxin MI. Trypsin and chymotripsin were used to cleave the peptide chains, leaving the disulfide bridges intact. Samples of 1–5 nmol of either natural or synthetic toxin were incubated in 5 microliters of 0.1 M ammonium acetate, pH 8.5, containing 0.5 microgram of the appropriate enzyme. After 4 hours at 37° C., the reactions were stopped by the addition of 180 microliters of 0.1% TFA. The digestion products were analyzed on the HPLC column, using 0.1% TFA—acetonitrile.

FIG. 3 shows the typical peak obtained at 25° C., during elution of synthetic conotoxin MI with 0.1% TFA—acetonitrile. The material had been isolated as a narrow cut from the sharp region (last fourth) of a similar peak. It appeared likely therefore, that the skewing was due either to degradation of the peptide, or to nonequilibrium behavior during elution.

To test the first possibility, material was isolated from the first third of a typical peak, and rerun under the same conditions. The complete profile was regenerated (FIG. 3b), eliminating peptide breakdown as the source of the skewing. We attempted also to improve the chromatographic behavior of the toxin, but no change was seen on testing a different reversed-phase column, Supelco LC18. The natural toxin gave peak profiles very similar to those of the synthetic material (FIG. 3c), and eluted at the same time. The synthetic and natural materials were identical as shown by their chromatographic behavior, by biological activity and by chromatography of enzymically cleaved peptides.

The strong *forward* skew of conotoxin MI peaks is interpreted as due to the occurrence of a slow interconversion between two or more forms of the peptide in solution, rather than non-equilibrium partitioning between free and bound phases. A five-fold increase in concentration of the ion pairing agent, to 0.5% TFA, led to the expected increase in retention time (FIG. 4a), but did not cause any obvious change of peak shape. Regardless of the cause of disequilibrium, an increased temperature was expected to improve peak shape, by speeding up the attainment of equilibrium. A marked improvement was obtained at 50° C. and 60° C. (FIGS. 4b and 4c). The latter conditions (0.5% TFA—acetonitrile, 60° C.) were used with the VYDAC column to purify both natural and synthetic conotoxin MI.

The two modes of non-equilibrium behavior should give different results upon lowering the temperature during chromatography. If disequilibrium is between sorption/desorption, one expects the problem to become worse at low temperature. By contrast, disequilibrium between two peptide conformations, when carried to an extreme, should lead to separation of two sharp peaks with an elevated baseline between them. Precisely this result was obtained by immersing the column in an ice-bath during chromatography of conotoxin MI (FIG. 5). Flow rate was 1.0 ml/mm and the gradient was 10(0)-10(1)-50(20). It is therefore concluded that the anomalous behavior is due to retarded equilibrium between conformational states of a single peptide.

By intraperitoneal assay in mice, the specific activities of the natural and synthetic MI toxins were indistinguishable. Both were somewhat more active than conotoxin GI, having an activity of 2.2 units per nmol. This corresponds to an $LD_{50}$ of approximately 12 micrograms/Kg. It is possible that the biological activities of the two conformational states may differ. The fact that such conformation states exist at all is surprising in view of the constrained, bicyclic configuration of the toxin. It is clear that biological activity is present in the conformation or equilibrium mixture of conformations present under physiological conditions.

EXAMPLE 7

Synthesis and activity of desGlu-GI. Synthetic conotoxin GI was treated by phenylisothiocyanate degradation (Tarr, G. E., *Anal. Biochem.*, 63, 361 (1975) to remove the N-terminal amino acid. The shortened peptide was purified by HPLC, as described in Example 6, supra. Amino acid analysis of material in the major peak showed no glutamic acid; maximal contamination by unmodified GI was about 1%. Bioassay, as described (Example 6), of conotoxin desGlu-GI gave a measured specific activity essentially equal to that of natural conotoxin GI.

EXAMPLE 8

Halogenated conotoxin derivatives. Synthetic conotoxin GI was iodinated at pH 5.3, pH 8 or pH 9.5 with sodium iodide, using "iodogen" as the oxidizing agent, essentially as described by Fraker, P. J., et al, *Biophys. Res. Comm.*, 80, 849 (1978). Products were separated by HPLC. Excellent separations were obtained, in which increasing retention times were found for products with increasing degree of substitution. Chlorination was carried out by excess of iodogen in the reaction mixture. The products were characterized by amino acid analysis. Biological activities for active derivatives were measured and are here expressed as relative toxicities, on a molar basis, compared with conotoxin GI.

| Conotoxin | Relative Activity |
|---|---|
| GI | 1.00 |
| monoiodoTyr-GI | 0.40 |
| diiodoTyr-GI | 0.35 |
| monochloro-monoiodoTyr-GI | 0.68 |
| monoiodoHis-diiodoTyr-GI | 0.50 |

What is claimed is:
1. A peptide having the structure

$$U-Cys-Cys-V_4-V_5-V_6-Cys-W-X-Y-Z-V_{12}-Cys-R$$

with S—S bridges from the first Cys to the third Cys and from the second Cys to the fourth Cys, wherein
U is —$NH_2$, Glu, Asp, Gly—Arg, N-trimethyl Glu or N-trimethyl Asp,
any of $V_4$, $V_5$ or $V_6$ is Asn, His, Pro or Ala,
$V_{12}$ is Ser or Cys,
W is Gly,
X is Lys, Arg, ornithine, homoarginine, N-methyl lysine, dimethyl lysine or trimethyl lysine, Y is Asn, Phe, Tyr, nitrotyrosine, His, Trp, monoiodo His, or substituted Phe,
Z is Leu, Val, Ile, Phe, Tyr, monoido Tyr, diiodo Tyr, monochloro-monoiodo Tyr, or cyclohexylalanine, and
R is —NH$_2$, —Gly—Lys—NH$_2$.

2. A peptide according to claim 1 wherein
U is Glu, Gly—Arg, or NH$_2$,
V$_4$ is Asn or His,
V$_5$ is Pro,
V$_6$ is Ala,
W is Gly,
X is Arg or Lys,
Y is His, Asn, or monoiodo His, or diiodo His,
Z is Tyr, Phe, monoiodo Tyr, diiodo Tyr, or monochloro-monoiodo Tyr,
V$_{12}$ is Ser, and
R is —NH$_2$ or Gly—Lys—NH$_2$.

3. A peptide according to claim 1, comprising conotoxin GI.

4. A peptide according to claim 1, comprising conotoxin GII.

5. A peptide according to claim 1, comprising conotoxin GIA.

6. A peptide according to claim 1, comprising conotoxin MI.

7. A peptide according to claim 1, comprising conotoxin desGlu-GI.

8. A peptide according to claim 1, comprising conotoxin monoiodo Tyr$_{11}$—GI.

9. A peptide according to claim 1, comprising conotoxin diiodo Tyr$_{11}$—GI.

10. A peptide according to claim 1, comprising conotoxin monochloro-monoiodo Tyr$_{11}$—GI.

11. A peptide according to claim 1, comprising conotoxin monoiodo His$_{10}$ diiodo Tyr$_{11}$—GI.

12. A peptide having the structure $$U-Cys-Cys-V_4-V_5-V_6-Cys-W-X-Y-Z-V_{12}-Cys-R$$

with S—S bridge between Cys residues, and S (acetamidomethyl) on two Cys residues.

wherein
U is —NH$_2$, Glu, Asp Gly—Arg, N-trimethyl Glu or N-trimethyl Asp,
any of V$_4$, V$_5$ or V$_6$ is Asn, His, Pro or Ala,
V$_{12}$ is Ser or Cys,
W is Gly,
X is Lys, Arg, ornithine, homoarginine, N-methyl lysine, dimethyl lysine or trimethyl lysine,
Y is Asn, Phe, Tyr, nitrotyrosine, His, Trp, monoiodo His or substituted Phe,
Z is Leu, Val, Ile, Phe, Tyr, monoiodo Tyr, diiodo Tyr, monochloro-monoiodo Tyr, or cyclohexylalanine, and
R is —NH$_2$, —Gly—Lys—NH$_2$.

13. A peptide according to claim 12 wherein
U is Glu, Gly—Arg or NH$_2$,
V$_4$ is Asn or His,
V$_5$ is Pro,
V$_6$ is Ala,
W is Gly,
X is Arg or Lys,
Y is His, Asn or monoiodo His,
Z is Tyr, Phe, monoiodo Try, diiodo Tyr, monochloro-monoiodo Tyr,
V$_{12}$ is Ser, and
R is —NH$_2$ or Gly—Lys—NH$_2$.

14. A peptide having the structure $$U-Cys-Cys-V_4-V_5-V_6-Cys-W-X-Y-Z-V_{12}-Cys-R$$

with S—S bridge between Cys residues, and S-(acetamidomethyl) on two Cys residues.

wherein
U is —NH$_2$, Glu, Asp, Gly—Arg, N-trimethyl Glu or N-trimethyl Asp,
any of V$_4$, V$_5$ or V$_6$ is Asn, His, Pro and Ala,
V$_{12}$ is Ser or Cys,
W is Gly,
X is Lys, Arg, ornithine, homoarginine, N-methyl lysine, dimethyl lysine or trimethyl lysine,
Y is Asn, Phe, Tyr, nitrotyrosine, His, Trp, monoiodo His or substituted Phe,
Z is Leu, Val, Ile, Phe, Tyr, monoiodo Tyr, diiodo Tyr, monochloro-monoiodo Tyr, or cyclohexylalanine, and
R is —NH$_2$, —Gly—Lys—NH$_2$.

15. A peptide according to claim 14 wherein
U is Glu, Gly—Arg or NH$_2$,
V$_4$ is Asn or His,
V$_5$ is Pro,
V$_6$ is Ala,
W is Gly,
X is Arg or Lys,
Y is His, Asn or monoiodo His,
Z is Tyr, Phe, monoiodo Try, diiodo Tyr, monochloro-monoiodo Tyr,
V$_{12}$ is Ser, and
R is —NH$_2$ or Gly—Lys—NH$_2$.

* * * * *

UNITED STATES PATENT AND TRADEMARK OFFICE
CERTIFICATE OF CORRECTION

PATENT NO. : 4,447,356
DATED : May 8, 1984
INVENTOR(S) : Baldomero M. OLIVERA, Lourdes J. CRUZ, William M. GRAY & Jean E.F. RIVIER It is certified that error appears in the above-identified patent and that said Letters Patent is hereby corrected as shown below:

IN THE ABSTRACT:

In line 6, the word "lacing" should be deleted and replaced with -- having --.

Signed and Sealed this

Twenty-fifth Day of September 1984

[SEAL]

Attest:

GERALD J. MOSSINGHOFF

Attesting Officer

Commissioner of Patents and Trademarks